United States Patent
Lalpuria et al.

(10) Patent No.: US 8,974,732 B2
(45) Date of Patent: Mar. 10, 2015

(54) METHOD FOR MEASURING THE AREA OF A SAMPLE DISPOSED WITHIN AN ANALYSIS CHAMBER

(71) Applicant: Abbott Point of Care, Inc., Princeton, NJ (US)

(72) Inventors: Niten V. Lalpuria, Mumbai (IN); Stephen C. Wardlaw, Lyme, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 50 days.

(21) Appl. No.: 13/692,611

(22) Filed: Dec. 3, 2012

(65) Prior Publication Data

US 2013/0203107 A1    Aug. 8, 2013

Related U.S. Application Data

(62) Division of application No. 12/421,293, filed on Apr. 9, 2009, now Pat. No. 8,326,008.

(60) Provisional application No. 61/043,567, filed on Apr. 9, 2008.

(51) Int. Cl.
| | |
|---|---|
| *G01N 15/06* | (2006.01) |
| *G01N 33/00* | (2006.01) |
| *G01N 33/48* | (2006.01) |
| *G01N 21/17* | (2006.01) |
| *G06T 7/00* | (2006.01) |
| *G06T 7/60* | (2006.01) |

(52) U.S. Cl.
CPC .............. *G01N 21/17* (2013.01); *G06T 7/0012* (2013.01); *G06T 7/602* (2013.01); *G06T 2207/10056* (2013.01); *G06T 2207/10064* (2013.01); *G06T 2207/30024* (2013.01)

USPC ........... 422/68.1; 422/50; 422/82.05; 422/58; 422/73; 436/43; 436/63; 436/66; 436/69; 436/164; 356/244; 356/246

(58) Field of Classification Search
CPC ....... G01N 33/48; G01N 33/00; G01N 21/76; G01N 21/29; G01N 15/06
USPC ................ 422/50, 68.1, 82.05, 58, 73, 82.06, 422/82.08; 436/43, 63, 66, 69, 70, 164, 436/165, 169, 172; 356/244, 246
See application file for complete search history.

(56) References Cited

U.S. PATENT DOCUMENTS

| | | | | | |
|---|---|---|---|---|---|
| 4,453,266 | A | * | 6/1984 | Bacus | ........................... 382/134 |
| 5,594,808 | A | * | 1/1997 | Shen et al. | .................... 382/133 |
| 5,835,620 | A | * | 11/1998 | Kaplan et al. | ................. 382/133 |
| 6,730,521 | B1 | * | 5/2004 | Cassells | ........................ 436/523 |

(Continued)

*Primary Examiner* — Brian J Sines
(74) *Attorney, Agent, or Firm* — O'Shea Getz P.C.

(57) ABSTRACT

A method for determining the area of an analysis chamber covered by a biologic fluid sample quiescently residing within the chamber is provided. The chamber has a first panel with an interior surface, and a second panel with an interior surface, both of which panels are transparent. The method includes the steps of: a) illuminating the sample residing within the analysis chamber at one or more wavelengths operable to highlight interfaces between the sample and air, and to highlight a constituent within the sample; b) imaging the sample along the one or more wavelengths, and producing image signals representative of the interaction of the one or more wavelengths with the sample; c) determining a location of at least one interface between the sample and air, using the image signals; d) determining a location of one or more constituents within the sample relative to the at least one sample-air interface using the image signals; and e) determining an area of the chamber containing the sample, using the location of the one or more constituents and the at least one sample-air interface.

4 Claims, 5 Drawing Sheets

(56) References Cited

U.S. PATENT DOCUMENTS

| | | | |
|---|---|---|---|
| 6,929,953 B1 * | 8/2005 | Wardlaw | 436/63 |
| 7,561,267 B2 * | 7/2009 | Luo et al. | 356/336 |
| 2002/0028158 A1 * | 3/2002 | Wardlaw | 422/82.05 |
| 2007/0087422 A1 * | 4/2007 | Riva et al. | 435/136 |

* cited by examiner

METHOD FOR MEASURING THE AREA OF A SAMPLE DISPOSED WITHIN AN ANALYSIS CHAMBER

The present application is a divisional of U.S. patent application Ser. No. 12/421,293 filed Apr. 9, 2009, which claims priority to U.S. Provisional Patent Application Ser. No. 61/043,567, filed Apr. 9, 2008.

BACKGROUND OF THE INVENTION

1. Technical Field

The present invention relates to methods for analysis of biologic fluid samples general, and apparatus and methods for determining the area filled by the sample within an analysis chamber in particular.

2. Background Information

Physicians, veterinarians and scientists have examined human and animals' biologic fluids, especially blood, in order to determine constituent quantities as well as to identify the presence of unusual particulates not seen in healthy subjects. The constituents generally measured, quantified and identified include red blood cells (RBCs), white blood cells (WBCs), and platelets.

Known blood examination techniques, described in detailed medical texts such as Wintrobe's Clinical Hematology 12$^{th}$ Edition, generally divides the examination methods into manual, centrifugal, and impedance type methods. Manual methods typically involve the creation of an accurately determined volume of a blood or fluid sample that is quantitatively diluted and visually counted in a counting chamber. Manual examination methods include examining a peripheral smear where the relative amounts of the particulate types are determined by visual inspection. Centrifugal examination methods involve centrifuging the sample, causing the sample to separate into constituent layers according to the relative densities of the constituents. The component layers can be stained to enhance visibility or detection Impedance methods involve the examination of an accurate volume of blood which is treated according to the particulate being measured; e.g., lysing RBCs for enumeration of the nucleated cells and volumetrically diluting the sample in a conductive fluid. The process typically involves monitoring a current or voltage applied to sample passing through a narrow passage to determine the effect particulates have on the current/voltage as the particulates pass through in single file. Other techniques involve analyzing the intensity and angle of scatter of light incident to particulates passing single file through a light beam.

All of the aforementioned methods, other than the peripheral smear or centrifugal separation, require dispensing a precise volume of sample. Inaccuracies in the sample volume will result in quantitative errors of the same magnitude in the associated analysis. With the exception of centrifugal methods, all of the aforementioned methods also require the sample to be mixed with one or more liquid reagents or diluents, and also require calibration of the instrument to obtain accurate results. In the case of peripheral smears, a high degree of training is needed to properly examine the smear. A number of the aforementioned methods generate large volumes of contaminated waste which is expensive to handle.

SUMMARY OF THE INVENTION

According to an aspect of the present invention, a method for determining the area of an analysis chamber covered by a biologic fluid sample quiescently residing within the chamber is provided. The chamber has a first panel with an interior surface, and a second panel with an interior surface, both of which panels are transparent. The method includes the steps of: a) illuminating the sample residing within the analysis chamber at one or more wavelengths operable to highlight interfaces between the sample and air, and to highlight a constituent within the sample; b) imaging the sample along the one or more wavelengths, and producing image signals representative of the interaction of the one or more wavelengths with the sample; c) determining a location of at least one interface between the sample and air, using the image signals; d) determining a location of one or more constituents within the sample relative to the at least one sample-air interface using the image signals; and e) determining an area of the chamber containing the sample, using the location of the one or more constituents and the at least one sample-air interface.

An analysis chamber having a pair of transparent panels separated by a uniform height provides a convenient vehicle for the analysis of the sample. For many analyses, it is useful (or required) to know the volume of the sample being analyzed, but difficult to dispense an accurately known amount of sample. To avoid the problem of dispensing accurately known amounts of sample, it would be useful to measure the area of the film generated in the aforesaid analysis chamber and multiplying that area by the chamber height to determine the sample volume added. If the blood (or other biologic fluid) would distribute in geometrically perfect shapes, this would be relatively easy, but samples, as they spread through the chamber from their point of application, often trap air bubbles or have serpentiginous edges. The task of determining the area of a sample within a chamber is particularly problematic for blood samples having a low number of red blood cells, where the relatively clear plasma will separate from the majority of the sample, and this relatively colorless area may not be included in the area calculations if the coloration of the sample area is the only criteria used for its area calculation. The present method provides an accurate way of determining sample area and therefore volume in a chamber of uniform height, and thereby provides a solution to the problems associated with dispensing an accurate sample volume.

The present method and advantages associated therewith will become more readily apparent in view of the detailed description provided below, including the accompanying drawings.

DETAILED DESCRIPTION OF EMBODIMENTS OF THE INVENTION

The present invention provides one or more methods for determining the area of a biological fluid sample quiescently residing within an analysis chamber. Depending on the analysis, the sample area itself can provide desirable, useful information. In other analyses, the area can be used to determine the volume of the sample within the chamber; e.g., where the chamber height is known or is determinable, the sample volume sample can be determined using the area and the known or determinable height of the chamber.

The present method(s) can be performed with an analysis chamber that is operable to quiescently hold a biological fluid sample (e.g., a sample of substantially undiluted anticoagulated whole blood) for analysis. The chamber is typically sized to hold about 0.2 µl to 1.0 µl of sample, but the method is not limited to use with any particular chamber volume, and the chamber volume can vary to suit the analysis application. In those instances when the present method is performed on a sample of whole blood disposed within a chamber, the sample is typically "substantially undiluted", meaning that the blood sample has either not diluted at all or has not been diluted purposefully, but has had some reagents added thereto for purposes of the analysis. To the extent the addition of the reagents dilutes the blood sample, if at all, such dilution has no clinically significant impact on the analysis performed. An example of a reagent that may be used with blood sample is an anticoagulant (e.g., EDTA, heparin), which is typically added in dried form and is not intended to dilute the sample. Anticoagulants are not required for all blood analyses, however. Under certain circumstances (e.g., very rapid analysis—such as may happen when blood is drawn from a patient finger stick or a neonatal heel-stick), it may not be necessary to add the anticoagulating agent. The term "quiescent" is used herein to describe that the sample is deposited within the chamber for analysis, and is not purposefully moved relative to the chamber during the analysis. To the extent that motion is present within the blood sample, it will predominantly be due to Brownian motion of the blood sample's formed constituents, which motion is not disabling of the use of the device of this invention.

Figure 1:
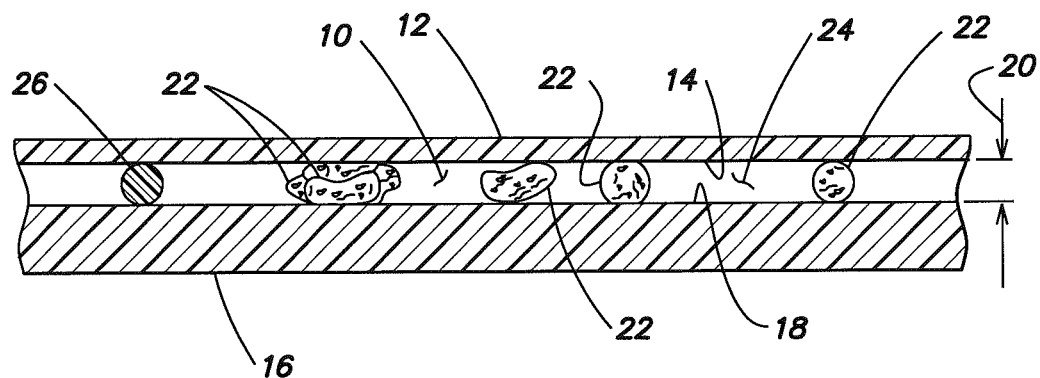
FIG. 1 is a diagrammatic sectional view of an analysis chamber containing a blood sample.
Figure 2:
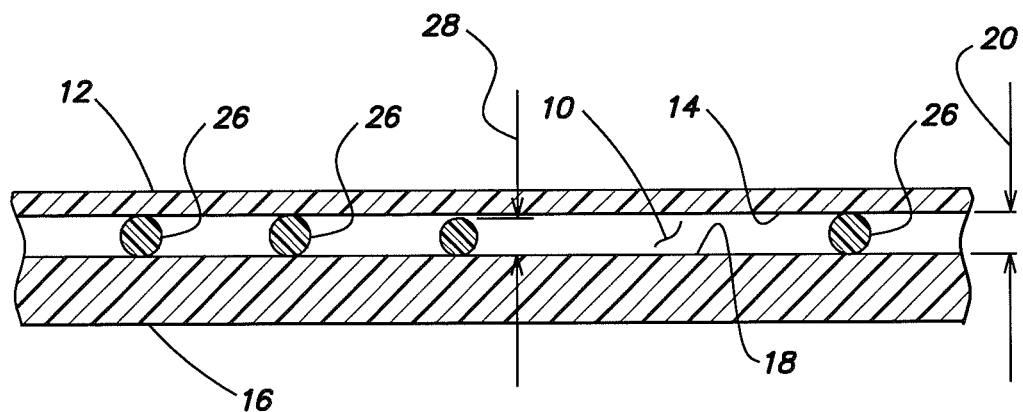
FIG. 2 is a diagrammatic sectional view of an analysis chamber embodiment.
Figure 3:
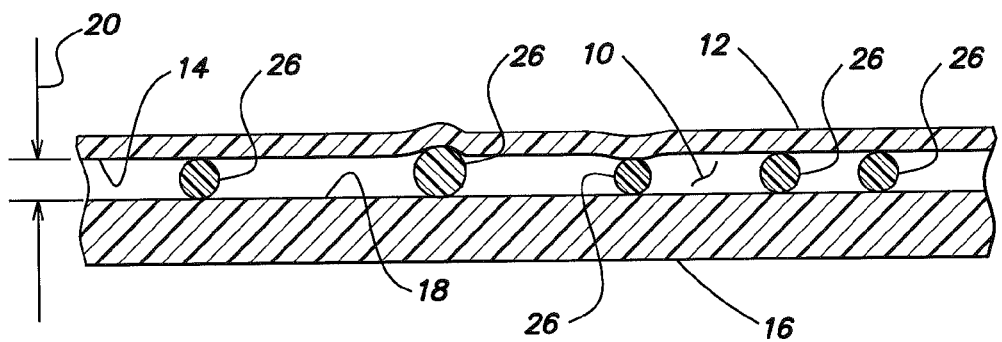
FIG. 3 is a diagrammatic sectional view of an analysis chamber embodiment.

Now referring to FIGS. 1-3, an example of an acceptable analysis chamber 10 is one that includes a first panel 12 having an interior surface 14, and a second panel 16 having an interior surface 18. The panels 12, 16 are both sufficiently transparent to allow the transmission of light along predetermined wavelengths there through in an amount sufficient to perform the analysis described below. In preferred embodiments, at least portions of the panels 12, 16 are parallel with one another, and within those portions the interior surfaces 14, 18 are separated from one another by a height 20, which height may be known or measurable. An analysis chamber having parallel panels 12, 16 is preferred for at least the reason that the uniform chamber height facilitates a sample volume determination. Parallel chamber panels are not required to determine the sample area, or to determine the sample volume, however; e.g., a chamber having one panel disposed at a known non-parallel angle relative to the other panel could be used.

The chamber 10 shown in FIGS. 1-3 includes at least three separators 26 disposed between the panels 12, 16. The separators 26 can be any structure that is disposable between the panels 12, 16, operable to space the panels 12, 16 apart from one another. The heights 28 of the separators 26 typically do not equal one another exactly (e.g., manufacturing tolerances), but are within commercially acceptable tolerance for spacing means used in similar analysis apparatus. Spherical beads are an example of an acceptable separator 26 and are commercially available from, for example, Bangs Laboratories of Fishers, Ind., U.S.A.

Figure 4:
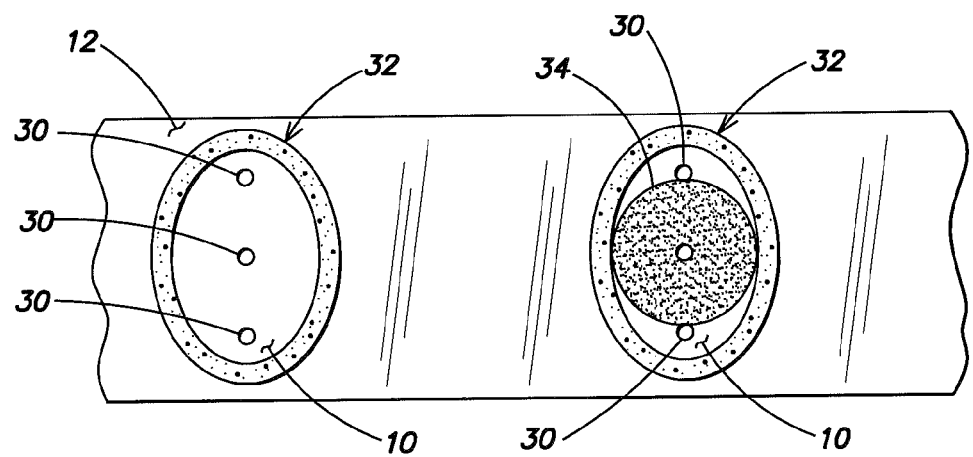
FIG. 4 is a diagrammatic sectional view of an analysis chamber embodiment.

In the chamber embodiment shown in FIG. 2, the separators 26 consist of a material that has greater flexibility than one or both of the first panel 12 and the second panel 16. As can be seen in FIG. 2, the larger separators 26 are compressed to the point where most separators 26 are touching the interior surfaces of the panels 12, 16, thereby making the chamber height just slightly less than the mean separator 26 diameters. In the chamber embodiment shown in FIG. 3, the separators 26 consist of a material that has less flexibility than one or both of the first panel 12 and the second panel 16. In FIG. 3, the first panel 12 is formed from a material more flexible than the spherical separators 26 and the second panel 16, and will overlay the separators 26 in a tent-like fashion. In this embodiment, although small local regions of the chamber 10 may deviate from the desired chamber height 20, the average height 20 of the chamber 10 will be very close to that of the mean separator 26 diameter. Analysis indicates that the mean chamber height 20 can be controlled to one percent (1%) or better at chamber heights of less than four microns using this embodiment. Subject to the flexibility characteristics described above, the separators 26 and panels 12, 16 can be made from a variety of materials, provided the panels 12, 16 are sufficiently transparent. Transparent plastic films consisting of acrylic or polystyrene are examples of acceptable panels 12, 16, and spherical beads made of polystyrene, polycarbonate, silicone, and the like, are acceptable separators 26. Referring to FIG. 4, the panel 12 that is to be vertically disposed above the other includes a plurality of ports 30 disposed at regular intervals (e.g., at least some of which can act as an air vent), and the panels 12, 16 are bonded together at points. In some embodiments, the bonding material 32 forms an outer chamber wall operable to laterally contain the sample 34 within the analysis chamber 10. In other embodiments, one or both panels 12, 16 can have a hydrophobically modified surface that operates like a chamber wall to laterally contain the sample within the analysis chamber 10. The bonding material or the hydrophobically modified surface may include a sensible colorant that can be used to identify the location of the chamber periphery. Examples of an acceptable analysis chamber are described in greater detail in U.S. Patent Application Publication Nos. 2007/0243117, 2007/0087442, and U.S. Pat. No. 6,723,290, all of which are hereby incorporated by reference in their entirety. The present method is not, however, limited to these particular chamber embodiments.

The analysis of the sample quiescently disposed within the chamber 10 is performed using an analysis device that is operable to illuminate and image at least a portion of the sample and perform an analysis on the image. The image is produced in a manner that permits one or both of the light absorbance through, and fluorescent emissions from, at least a portion of the sample to be determined on a per image unit basis. The term "per image unit basis" means an incremental unit of which the image of the sample can be dissected. A pixel which is generally defined as the smallest element of an image that can be individually processed within a particular imaging system is an example of an image unit, and an image unit may also include a small number of pixels in a collective unit. The magnification of an imaging device can also be described in linear terms (e.g., microns per pixel at the focal plane), where the linear dimension is along a particular axis of an orthogonal grid applied to the image. The actual area of the sample captured by pixels of the sensor at the focal plane is therefore a function of the magnification factor applied by the imaging device. Hence, the magnification of the imaging device should be known or determinable. The volume associated with that pixel is therefore the area of the image per pixel times the known chamber height. For example if the magnification was 0.5 microns per pixel, an image occupying 200 pixels would have an area of 50 square microns, and a volume of 50 square microns times the chamber height.

Figure 5:
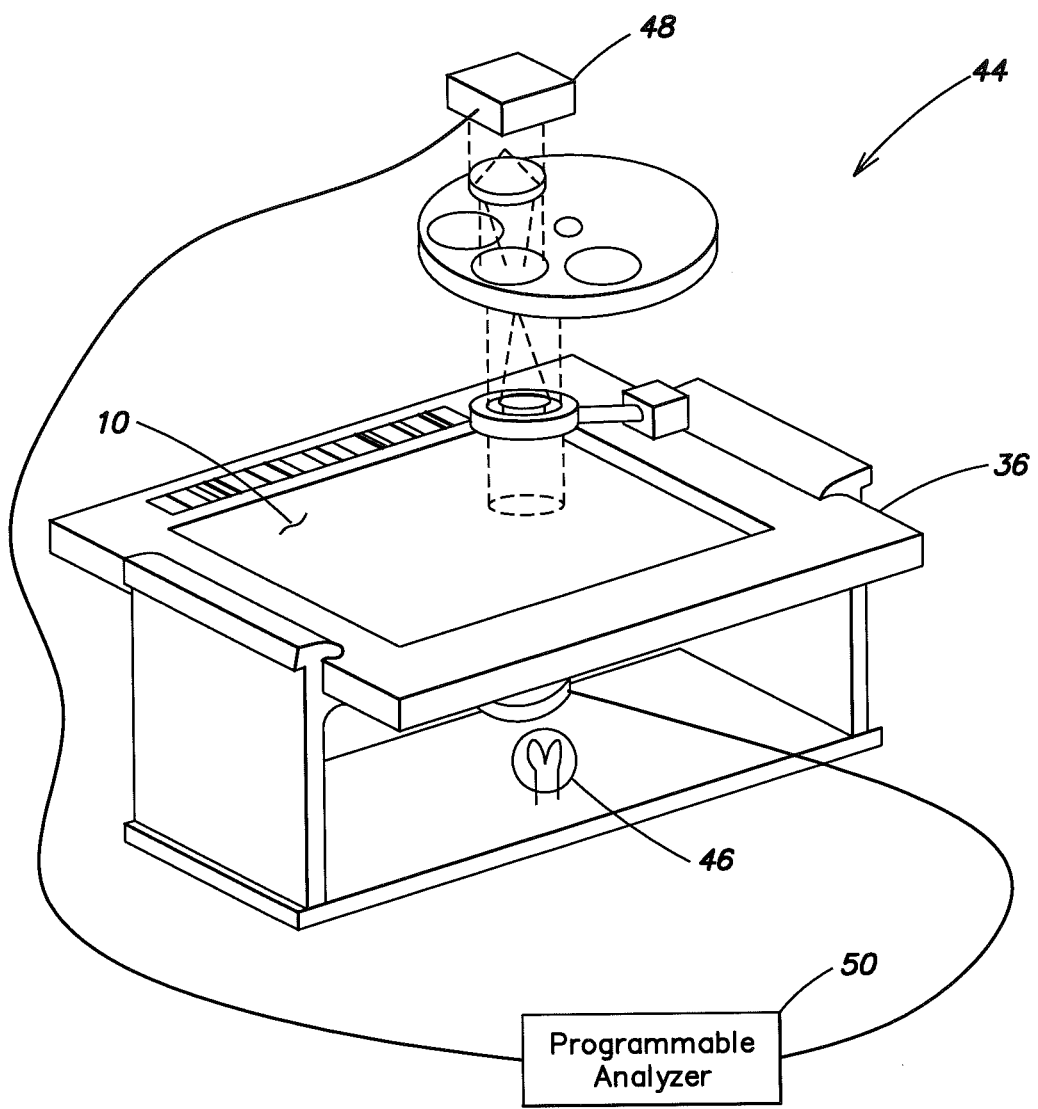
FIG. 5 is a diagrammatic planar view of an analysis chamber.

Now referring to FIG. 5, an example of an analysis device 44 that can be adapted for use with the present method includes a sample illuminator 46, an image dissector 48, and a programmable analyzer 50. The sample illuminator 46 selectively produces light along certain desired wavelengths using either a source that emits light along particular desired wavelengths (e.g., LEDs) or that emits light along a broad wavelength range. An illuminator 46 operable to produce light at about 413 nm and about 540 nm is particularly useful for analyzing blood samples because of the substantial light absorption that occurs within the hemoglobin at these wavelengths (i.e., a high molar extinction coefficient (s) at the aforesaid wavelengths). The absorption of the light is a type of "interaction" between the wavelengths of light and the sample. The sample illuminator 46 can be configured to produce the light in a transmittance mode, or in an epi-illumination mode, or both, relative to the chamber 10, and the sample illuminator 46 is operable to illuminate some, or all, of the sample residing within the chamber 10. In the transmittance mode, a light source portion of the sample illuminator 46 is positioned on one side of the sample residing within the chamber 10 and directing the light through the sample quiescently disposed between chamber panels, and thereafter to the image dissector 48.

An example of an acceptable image dissector 48 is a charge couple device (CCD) that converts an image of the light passing through the sample into an electronic data format (i.e., a signal). Complimentary metal oxide semiconductor ("CMOS") type image sensors are another example of an image sensor that can be used, and the present invention is not limited to either of these examples.

The programmable analyzer 50 includes a central processing unit (CPU) and is connected (at least electronically and/or optically) to the sample illuminator 46 and image dissector 48. The CPU is adapted (e.g., programmed) to selectively perform the functions necessary to carry out the present method. It should be noted that the functionality of programmable analyzer may be implemented using hardware, software, firmware, or a combination thereof. A person skilled in the art would be able to program the processing unit to perform the functionality described herein without undue experimentation. U.S. Pat. No. 6,866,823 entitled "Apparatus for Analyzing Biologic Fluids" and issued Mar. 15, 2005, which is hereby incorporated by reference in its entirety, discloses such an analysis device.

The analysis device 44 is adapted to: 1) illuminate the sample disposed within the analysis chamber at one or more wavelengths operable to highlight interfaces between the sample and air and at least one constituent within the sample; 2) image the sample along the wavelengths, and produce image signals representative of the interaction of the wavelengths with the sample; and 3) determine at least one interface between the sample and air, using the image signals.

In some embodiments, the analysis device 44 is further adapted to determine at least one sample region and at least one no-sample region, separated from one another by one or more sample-air interfaces. Each sample region contains at least one constituent from the sample. Each no-sample region does not contain a constituent from the sample. The spatial relationship involving sample regions, no-sample regions, and sample-air interfaces may be described such that a sample region is disposed on a first side of a sample-air interface and a no-sample region disposed on a second side of the same sample-air interface, wherein the first and second sides are "opposite" one another. It should also be noted that the geometries of the sample and no-sample zones can widely vary and are rarely limited to a single line of demarcation; e.g., samples often contain air bubbles, etc. Consequently, the sample regions and no-sample regions may also be described as complementing each other within the analysis chamber. As indicated above, constituents within a blood sample include, but are not limited to, red blood cells (RBCs), white blood cells (WBCs), and platelets. If a sensible dye is admixed with plasma, which dye makes the presence of plasma readily discernible, then plasma may also be considered a constituent of a blood sample. In these embodiments, the analysis device 44 is further adapted to determine an area of the chamber containing the sample, using at least one of a sample regions and a no-sample region.

In other embodiments, the analysis device is adapted to: 1) locate constituents within the sample, and to provide a digital masking that masks one of the sample or no-sample regions; and 2) determine an area of the chamber containing the sample, using the masked area. The term digital masking as used herein refers to a binary imaging process wherein the image units (e.g., pixels) in an identified area (e.g., a sample region) are all given a particular value to distinguish those image units, from the image units containing the image values representative of the imaged illuminated sample. The masked image units, which are readily distinguishable, can then be further processed; e.g., summed to determine an area.

In other embodiments, the present invention includes a colorant deposited on at least one interior surface of the chamber. The colorant (e.g., a fluorescent dye such as acridine orange) admixed with the sample can be sensed using illumination, and can be used to determine the sample-air interfaces. In those instances where a fluorescent colorant is used, the sensible signal is a fluorescent emission at a particular wavelength created by a light source exciting the fluorescent colorant at another wavelength. The creation of the fluorescent emission may be described as a result of the "interaction" of the light used to illuminate the sample.

The following examples of the present method are described in the context of the present method applied to a sample of anti-coagulated whole blood placed between the two transparent panels of a chamber, which panels are separated by a uniform height. These examples are provided to illustrate the utility of the present method, and the present method should not be construed as being limited thereto and in particular should be construed as being limited to area determination of a whole blood sample.

Figure 6:
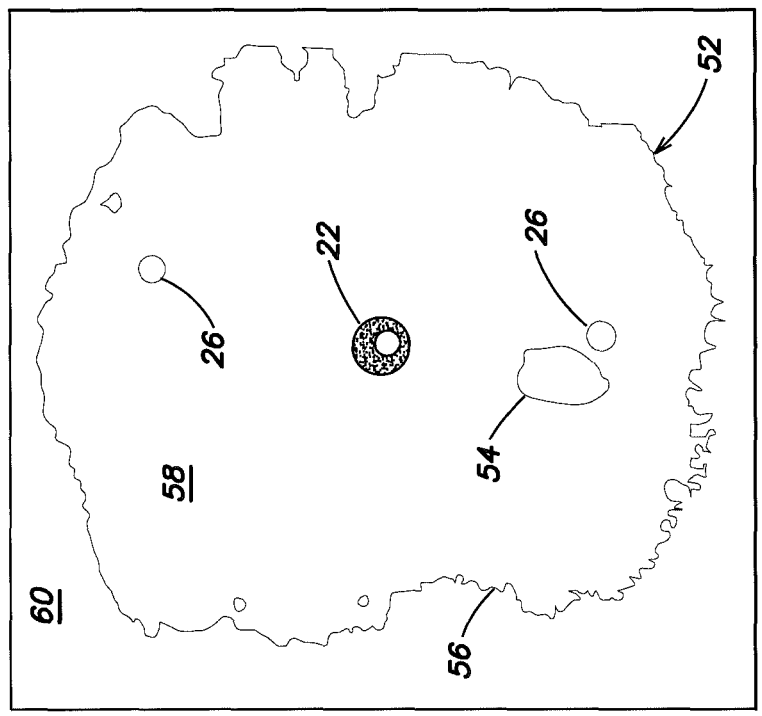
FIG. 6 is a diagrammatic image of a blood sample disposed within a chamber, illuminated to highlight red blood cells disposed within the sample.

In one embodiment of the method, the sample is illuminated and imaged using a plurality of wavelengths of light. One or more of the wavelengths chosen will highlight one or more target constituents within the image of the sample. For whole blood, a wavelength that is either around 415 nm or around 540 nm can be used to effectively highlight RBCs because light at these wavelengths is absorbed well by hemoglobin contained within the red blood cells. "Highlighted" RBCs can be identified using a threshold optical density value that is indicative of light absorption associated with hemoglobin. Image units meeting or exceeding the predetermined optical density value (or less than the threshold if exclusionary techniques are used) are identified as aligned with a RBC. As an alternative to utilizing hemoglobin light absorption, certain RBCs and other constituents (e.g., WBCs and platelets) can be highlighted with a fluorescent colorant (e.g., acridine orange) or other sensible colorant admixed with the sample. An advantage of using RBCs as a "target" constituent within a blood sample is that in relative terms, RBCs are the most populous constituents within the blood sample and consequently more likely to be found in any particular region containing sample. FIG. 6 is an image of a blood sample 52 disposed within a chamber, wherein RBCs 22 have been highlighted. The image includes a pair of separator particles 26, a RBC 22, and a plurality of air pockets 54.

Figure 7:
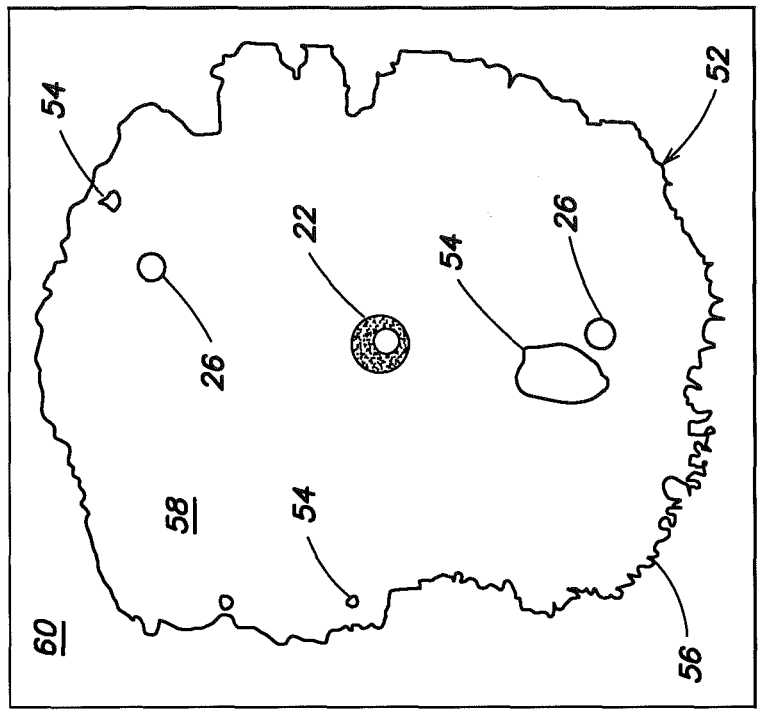
FIG. 7 is a diagrammatic image of a blood sample disposed within a chamber as shown in FIG. 6, illuminated to highlight the interfaces between the sample and air within the sample.

In this embodiment, the sample 52 is also illuminated with one or more wavelengths chosen to highlight the interface 56 between the sample 52 and the air. When the sample 52 is illuminated with this wavelength, the contents of the sample 52 are typically relatively colorless but the interface between the sample and the air is clearly identified by refraction of light at the wavelength that occurs at the sample-air interface 56. A wide variety of wavelengths can be used to identify the sample-air interface. When the biologic fluid being analyzed is whole blood, a wavelength at or above 600 nm, and more preferably about 700 nm, works well to highlight the sample-air interfaces. FIG. 7 is the blood sample image shown in FIG. 6, with the sample-air interfaces 56 now highlighted.

As stated above, a wide variety of wavelengths can be used to identify the sample-air interface 56. In some instances, wavelengths used to highlight the interfaces 56 can also be used to highlight the target constituents (e.g., RBCs 22) within the sample 52. As a result, the sample 52 can be imaged with light at a single wavelength, thereby obviating the need for providing light at two different wavelengths.

Biologic fluid samples disposed within an analysis chamber rarely have perfectly straight or curved sample-air interfaces 56. It is much more typical for a sample 52 to have a sample-air interface with an irregular, non-uniform geometry. A variety of techniques can be used to locate the sample-air interfaces within the chambers, and the present invention is not limited to any particular technique. For example, a segmentation technique can be used to identify image units (e.g., pixel) within the image having one or more particular characteristics (e.g., an image unit having a light intensity of x %); i.e., use the characteristics as identifying features. The pixels having those predetermined characteristics that are indicative of a sample-air interface 56 are identified and mapped relative to the sample chamber, thereby identifying their position within the image. Pixels having characteristics that are indicative of a target constituent (e.g., RBC 22) are also identified and located.

The relative positions of the one or more sample-air interfaces 56 and the target constituents (e.g., RBCs 22) define where the sample 52 is located and where it is not. Once the boundaries of the sample region(s) 58 and no-sample region(s) 60 are defined, the area of each region 58, 60 can be determined by summing the area associated with each image unit located within that particular region 58, 60. If the image unit areas within the sample region(s) 58 are summed, then the total area of the sample regions 58 represents the total area of the sample 52 disposed within the chamber. Note that in FIGS. 6-8, the sample is shown occupying a single sample region 58. In many instances, fluid samples can assume a plurality of independent sample regions 58 within a particular chamber.

Figure 8:
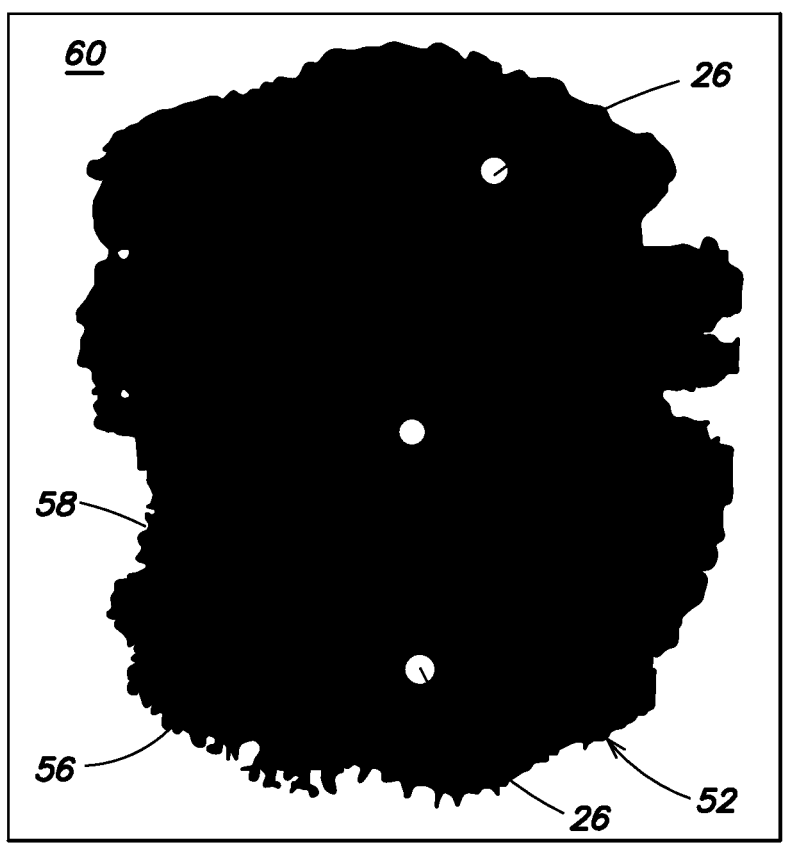
FIG. 8 is a diagrammatic image of a sample disposed within a chamber as shown in FIGS. 6 and 7, with the sample containing region digitally masked.

In another embodiment, once the sample-air interfaces 56 and the target constituents are located, the area can be determined using a digital binary masking technique that iteratively digitally masks image units within the sample regions. In one example of a digital binary masking procedure, image units contiguous with a constituent are masked in an iterative procedure, in directions extending out from the constituent until an already masked image unit, or a boundary of the chamber, is encountered. In addition, image units contiguous with a sample-air interface 56, on the constituent side of the interface are also masked in an iterative procedure, in a direction extending out from the interface 56 until an already masked image unit, or a chamber boundary, is encountered. The process iteratively continues until all or substantially all of the image units within that respective sample region are masked. FIG. 8 illustrates a masked version of the blood sample shown in FIGS. 6 and 7.

The present invention is not limited to the above-described example of a digital binary masking procedure mask. The masking procedure can alternatively mask the regions using image processing operations such as edge-location algorithms and the like.

The area of the sample region can be determined subsequently by summing the area associated with each masked image unit to arrive at the total area of the particular sample region. The total area of the sample regions represents the total area of the sample disposed within the chamber. The area of the sample regions can also be determined using a contrasting procedure if the total area of the imaged chamber is known or determinable. In such instances, the area of the no-sample regions can be masked and determined and then subtracted from the total imaged area to arrive at the sample region area. The total imaged area can be determined by summing the per image unit area of the entire image. If the total imaged area is symmetrically shaped, the area of a portion of the total imaged area can be determined and the appropriate multiplier can be subsequently applied to arrive at the total imaged area.

In some embodiments, the identification of the sample-air interfaces can be facilitated by applying a dried layer of sensible colorant within the chamber. Sample entering and traveling within the chamber picks up a disproportionate amount of the sensible colorant (i.e., acridine orange) at the sample-air interface. The concentration of sensible colorant at the sample-air interface highlights the interface and makes it easier to identify.

As indicated above, some analysis chambers include separator particles 26 to maintain a uniform chamber height 20. Such particles can be formed with characteristics (e.g., dyed) that make them readily discernible within the sample image. In the event such particles are disposed within a sample region, the area of each can be accounted for in the sample region area calculation (e.g., in the masked region shown in FIG. 8, the area associated with the separator particles 26 is not included in the masked area of the sample). The volume of the particles 26 within a masked area can also be accounted for given the known volume of the separators.

In an alternative embodiment, a chamber can be used having a portion bounded by one or more barriers that form a known area disposed therebetween. The barriers are separated by a distance, and positioned within the chamber, to increase the probability that the known area is filled with sample.

Although this invention has been shown and described with respect to the detailed embodiments thereof, it will be understood by those skilled in the art that various changes in form and detail may be made without departing from the spirit and scope of the invention.

What is claimed is:

1. An apparatus for analyzing a biologic fluid sample quiescently residing within an analysis chamber, which chamber has a first panel with an interior surface, and a second panel with an interior surface, at least one of which panels is transparent, comprising:
   a programmable analyzer comprising a processor adapted to:
      cause a sample illuminator connected to the programmable analyzer to non-obliquely illuminate the sample residing within the analysis chamber at one or more wavelengths, which wavelengths are operable to highlight interfaces between the sample and air, and to highlight at least one constituent within the sample;
      cause an image dissector connected to the programmable analyzer to image the sample along the one or more wavelengths non-obliquely illuminating the sample, and produce image signals representative of the interaction of the one or more wavelengths with the sample; and
      determine a location of at least one interface between the sample and air, using the image signals, and determine a location of one or more constituents within the sample relative to the at least one sample-air interface using the image signals, and determine an area of the chamber containing the sample, using the location of the one or more constituents and the at least one sample-air interface.

2. The apparatus of claim 1, wherein the analyzer is adapted to determine the area of the chamber containing the sample, using the location of the one or more constituents and the at least one sample/air interface, and is further adapted to define one or more sample regions, each containing one or more constituents, and one or more no-sample regions, each containing no constituents, wherein one of the at least one sample-air interfaces is disposed between each sample region and no-sample region.

3. The apparatus of claim 2, wherein the analyzer is adapted to determine the area of the chamber containing the sample by summing the area of the image units in each of the one or more sample regions.

4. The apparatus of claim 1, wherein the analyzer is adapted to determine a volume of the sample disposed within the chamber using the determined area of the chamber containing the sample, and a known chamber height.

* * * * *